(12) United States Patent
Miyazaki et al.

(10) Patent No.: US 6,562,323 B1
(45) Date of Patent: May 13, 2003

(54) COMPOSITE POWDER, COSMETIC AND PAINT WITH THE COMPOSITE POWDER BLENDED THEREIN

(75) Inventors: Takumi Miyazaki, Kitakyushu (JP); Hirokazu Tanaka, Kitakyushu (JP)

(73) Assignee: Catalysts & Chemicals Industries Co., Ltd., Kawasaki (JP)

( * ) Notice: Subject to any disclaimer, the term of this patent is extended or adjusted under 35 U.S.C. 154(b) by 93 days.

(21) Appl. No.: 09/672,507

(22) Filed: Sep. 29, 2000

(51) Int. Cl.⁷ .................. A61K 7/035; C08L 93/00; C09O 1/00; C04B 14/00
(52) U.S. Cl. .................. 424/69; 424/600; 106/241; 106/286.1; 106/286.8; 106/400; 525/902; 525/934
(58) Field of Search .................. 525/902, 934; 424/69, 600, 688; 106/241, 286.1, 286.8, 400

(56) References Cited

U.S. PATENT DOCUMENTS

| | | | | |
|---|---|---|---|---|
| 5,122,418 A | * | 6/1992 | Nakane et al. | 424/401 |
| 5,165,915 A | * | 11/1992 | Tokubo et al. | 424/63 |
| 5,182,103 A | * | 1/1993 | Nakane et al. | 424/78.03 |
| 5,356,617 A | * | 10/1994 | Schlossman | 424/63 |
| 5,628,934 A | * | 5/1997 | Ohno et al. | 252/586 |
| 5,762,913 A | * | 6/1998 | Tanaka et al. | 424/59 |
| 5,827,507 A | * | 10/1998 | Oshima et al. | 424/59 |
| 5,968,531 A | * | 10/1999 | Miyoshi et al. | 424/401 |
| 6,207,174 B1 | * | 3/2001 | Hineno et al. | 424/401 |

FOREIGN PATENT DOCUMENTS

| | | | |
|---|---|---|---|
| JP | 1-101377 | | 4/1989 |
| JP | 7-11161 | | 1/1995 |
| JP | 08-188723 | * | 7/1996 |
| JP | 8-209024 | | 8/1996 |

* cited by examiner

Primary Examiner—Russell Travers
Assistant Examiner—Lauren Q Wells
(74) Attorney, Agent, or Firm—Kanesaka & Takeuchi

(57) ABSTRACT

A composite powder prepared by coating a ramentaceous substrate with at least two color layers. A difference between the maximum value and the minimum value of the ab hue angle $h_{ab}$ ($h_{max}-h_{min}$) as defined in the recommendation on uniform color space by CIE is in the range from 10° to 180°. A ratio of the maximum value vs the minimum value of the brightness L* as defined in the recommendation is in the range from 1.0 to 2.0. According to the viewing angle, the color tone of the composite powder changes.

14 Claims, No Drawings

COMPOSITE POWDER, COSMETIC AND PAINT WITH THE COMPOSITE POWDER BLENDED THEREIN

TECHNICAL FIELD

The present invention relates to composite powder prepared by coating a ramentaceous substrate such as mica with two or more types of coloring layers. Moreover the present invention relates to cosmetic and paint with the composite powder blended therein.

BACKGROUND ART

Conventionally ramentaceous substrates such as mica, talc, a and sericite have been blended in cosmetics such as powder foundation or as pearl pigment in various types of paint such as paint for cars. The effect obtained when the ramentaceous powder is blended in cosmetic includes, but not limited to, improvement in the adaptability of the cosmetic to be spread on human skin, improvement of the color pigment of the dispersibility on human skin, and further improvement in the adhesiveness to human skin, and these characteristics are indispensable for make-up cosmetics.

For instance, mica covered with a titanium oxide layer having the certain thickness is called pearl pigment and is used in cosmetic and paint. This pearl pigment varies its color tone at a certain reflection angle against an incidence angle of light according to the thickness of the layer because of optical interference, and has intense luster. The more intense the luster, the more the brightness changes according to a viewing angle, and the characteristic is called flip-flop characteristic.

Colors generated because of the optical interference have the higher brightness as compared to those of general color pigments such as iron oxide red and ultramarine blue, but the tinting strength is very weak. As a method of improving the tinting strength, there has been proposed to cover the titanium oxide layer described above with a metal oxide which absorbs visible light having a wavelength in a certain range such as iron oxide (Refer to Japanese Patent Publication No. 7674/1983). With this method, however, although some particular colors are emphasized and the change in brightness caused by the luster can be made larger, but the effect that the color hue largely changes according to a viewing angle is rather weak.

In some cases, at first mica is covered with ferric oxide and then titanium oxide layer having the certain thickness is formed thereon, but also in this case the effect that the color tone largely changes according to a viewing angle is rather small (Refer to Japanese Patent Laid-Open Publication No. 11161/1995).

Japanese Patent Laid-Open Publication No. 101377/1989 proposes an invention relating to golden color luster pigment which is color and luster pigment containing mica or mica with metal oxide deposited thereon as a substrate and a metal oxide layer containing both titanium and iron coating the substrate, and also in which the metal oxide layer contains pseudo-blockite as an essential component. In this invention, it is described that the metal oxide layer containing, in addition to titanium and iron, pseudo-blockite as an essential component is used for coating the substrate to improve the stability against heat and chemical compounds, and the metal layer is not used for changing the color tone according to a viewing angle.

Japanese Patent laid-Open Publication No. 209024/1996 proposes luster pigment in which a flake-like substrate is sequentially coated with an achoromatic layer having the refractive index of 1.8 or below, a coating layer having the refractive index of 2.0 or more with selective absorbance, and an achromatic or selectively absorptive layer, if necessary, in this order, and there are enlisted aluminum and alloy thereof as the metal substrate; silica, aluminum oxide, and others as the material with the refractive index of 1.8 or below used to form the first layer; and iron oxide, chromium oxide, and titanium oxide ($TiO_2$ reduced with ammonia) as the material having the refractive index of 2.0 or more with selective absorbance. In this invention, the effect that the tone changes according to a viewing angle is pointed out, but in this luster pigment the metal substrate is used to intensify the tone change, and it is described in the publication that the pigment has intense metallic luster. Therefore, with the pigment, it is difficult to obtain cosmetics or paints having modest luster and natural appearance, and its concealing capability is disadvantageously too high.

DISCLOSURE OF THE INVENTION

An object of the present invention is to provide composite powder with the color tone changing according to a viewing angle and insuring natural appearance without excessive luster.

Another object of the present invention is to provide cosmetics and paints capable of emphasizing a face or other solid structures not with change in the brightness, but with change in the hue.

The present invention provides composite powder prepared by coating a ramentaceous substrate with at least two color layers characterized in that a difference between the maximum value and the minimum value of the ab hue angle $h_{ab}$ ($h_{MAX}-h_{MIN}$) as defined in the recommendation on uniform color spaces by CIE (Commission Internationale De L'eclairage) is in the range from 10° to 180° when this value exceeds 180°, the value of 360°−($h_{MAX}-h_{MIN}$) is in the range from 10° to 180°), and also that a ratio of the maximum value and the minimum value of the brightness L as defined in the recommendation is in the range from 1.0 to 2.0.

It is preferable to provide a transmission light dispersion layer with the refractive index of 1.3 to 1.8 between the color layers.

Also it is preferable to coat a surface of the composite powder with a reflection and dispersion layer with the refractive index of 1.3 to 1.8 and also having some irregularity on the surface.

Cosmetics and paints according to the present invention have any of the composite powders described above blended therein.

BEST MODE FOR CARRYING OUT THE INVENTION

Preferred embodiments of the present invention are described below.

(1) Composite Powder

A ramentaceous substrate is used for the composite powder according to the present invention. The ramentaceous substrate includes, but not limited to, natural minerals such as mica, talc, and sericite; and inorganic oxides such as syntheticmica, synthetic sericite, plate-like silica, plate-like aluminum oxide, and plate-like titanium oxide.

An average particle diameter of the ramentaceous substrate is preferably in the range from about 1 to about 100 μm, and more preferably in the range from 5 to 30 μm. When an average particle diameter of the ramentaceous substrate is less than 1 µm, and an average particle diameter of the obtained composite powder is less than 1 µm, change of hue hardly occurs, and on the contrary, when the average particle diameter of the ramentaceous substrate is more than 100 µm, and also the average diameter of obtained composite powder exceeds 100 µm, the luster is so intense that the appearance is unpleasant. The average particle diameter of the ramentaceous substrate as defined herein indicates an average value of the ramentaceous flat surfaces, which is obtained by 100 pieces of ramentaceous substrates with a scan type of electronic microscope for their maximum lengths and calculating the average value. Thickness of the ramentaceous substrate is preferably in the range from 0.05 to 1 µm.

As the color layer used for coating the substrate, known inorganic pigments, organic pigments, inorganic and organic composite pigments may be used, and in addition, coloring matters or a color layer colored with any coloring matter may be used.

More specifically inorganic pigments such as ferric oxide ($\alpha$-$Fe_2O_3$, $\gamma$-$Fe_2O_3$), oxi-iron hydroxide (FeO(OH)), ferric hydroxide ($Fe_2(OH)_6$), ferrous oxide (FeO), triiron tetraoxide ($Fe_3O_4$) titanium oxide containing iron oxide, carbon black, ultramarine blue, iron blue, titanium black, chromium hydroxide, lithium cobalt titanate, manganese violet; organic coloring materials including various types of tar coloring matters, natural coloring matters, and other synthetic coloring matters; and inorganic or organic material layers colored or stained with these inorganic or organic pigments can be enlisted.

There are no limitations as the sequence of lamination, color tone and so on of the color layers on the condition of different color tone each other, and at least two color layers selected likely may be laminated according to the use of composite powder.

In this process, thickness of each color layer is preferably in the range from 5 to 200 nm. When the thickness is less than 5 nm, the tinting power is not sufficient, and on the other hand, when the thickness is more than 200 nm, the feeling in touching is apt to become lower.

Of the sequentially laminated color layers, the first color layer is preferably in the range from 1 to 100 weight portions against 100 weight portions of the ramentaceous substrate, and more preferably in the range from 5 to 40 weight portions. When the quantity is less than 1 weight portion, the tinting power is insufficient, and if the quantity is over 100 weight portions, the adhesion to human skin and the feeling are apt to become lower when used as a component for cosmetics.

The second and subsequent layers are preferably in the range from 1 to 40 weight portions against the 100 weight portions of a ramentaceous substrate with the first color layer or with the first color layer and the transmission light dispersion layer formed thereon described below in the state where other color layer(s) and the transmission light dispersion layer are formed just before formation of the second and subsequent color layer. When the quantity of the second and subsequent layers is less than 1 weight portion, the tinting power is insufficient, and on the other hand, when the quantity is over 40 weight portions, the hiding capability is so strong that colors of underlying layers becomes invisible.

In the composite powder according to the present invention, it is required that a difference between the maximum value and the minimum value of the ab hue angle $h_{ab}$ ($h_{MAX}$–$h_{MIN}$) as defined in the recommendation on uniform color spaces by CIE (Commission Internationale De L'eclairage) is in the range from 10° to 180°. When the value ($h_{MAX}$–$I_{MIN}$) is over 180°, it is required that the value of 360°–($h_{MAX}$–$h_{MIN}$) is in the range from 10° to 180°. The value of hat is calculated through the following equation and by using color coordinates a*, b*:

$$h_{ab}=\tan^{-1}(b^*/a^*)$$

The reason the value of ($h_{MAX}$–$h_{MIN}$) or 360°–($h_{MAX}$–$h_{MIN}$) is limited to the above-described range is, when the value is outside the range, the cubic structure can not be emphasized by change in the hue, and a preferable range is decided according to an application of the composite powder. For instance, when used as a component for foundation which is cosmetic, the range from red to blue is preferable, so that the value of ($h_{MAX}$–$h_{MIN}$) or 360°–($h_{MAX}$–$h_{MIN}$) is in the range from 10° to 100°, and when used as a component of paint, the value is set in the range from 10° to 180°.

The difference between the maximum value and the minimum value of $h_{ab}$ is described more specifically below. For instance, when mica is used as a substrate, the first color layer is formed with red ferric oxide, and the second color layer is formed thereon with yellow titanium oxide containing iron oxide, yellow becomes stronger around the regular reflection angle, and red brown becomes stronger at farther points from the regular reflection angle. By blending the composite powder having the characteristics described above in cosmetics or paints, solid structure of a face or other physical portions can be emphasized not by change in the brightness, but with change in the hue.

In the composite powder according to the present invention, a ratio of the maximum value vs the minimum value of the brightness L* defined in the Recommendation on Uniform Color Spaces by CIE is required to be in the range from 1.0 to 2.0. The brightness L* is a scale for luster of the composite powder, and when the ratio of the maximum value vs the minimum value of the brightness L* is over 2.0, the luster is so intense that the natural appearance is lost.

The ab hue angle $h_{ab}$ and brightness L* are measured using the composite powder spread on adhesive surfaces of a highly smooth transparent double-faced tape adhered onto a white paper piece as a sample and the three-dimensional declination spectrometer (produced by Murakami Shikisai-Gijutsu Kenkyusho, GCMS-4 (based on the double beam system; light source: D65; and view angle: 10°)), and also by setting the incidence angle at 45° and changing the receiving angle from –80° to 80° at the measurement interval of 5°. In this present invention, assessment was made by calculating the difference ($h_{MAX}$–$h_{MIN}$) between the maximum value $h_{MAX}$ and the minimum value $h_{MIN}$ to $h_{ab}$. Also the assessment was made by calculating the ratio $L^*_{MAX}/L^*_{MIN}$ between the maximum value $L^*_{MAX}$ and the minimum value $L^*_{MIN}$ of the brightness L*. As the difference ($h_{MAX}$–$h_{MIN}$, between the maximum value $h_{MAX}$ and the minimum value $h_{MIN}$ of $h_{ab}$) is larger, the color changes substantially according to the viewing angle, and as the ratio $L^*_{MAX}/L^*_{MIN}$ is smaller, the luster is lower.

The composite powder according to the present invention should preferably have at least one transmission light dispersion layer with the refractive index in the range from 1.3 to 1.8 between the color layers. This transmission light dispersion layer disperses the light which has passed through the second color layer (upper layer) and comes into the transmission light dispersion layer, and also disperses the light which is reflected on the first color layer and comes again into the transmission light dispersion layer, so that it provides the effect intensifying the contrast between the color of the second color layer at angular positions near the regular reflection angle and the color of the first color layer at angular positions farther from the regular reflection angle. When the transmission light dispersion layer is not provided, the color of the second color layer at angular positions near the regular reflection angle and the color of the first color layer at angular positions farther from the regular reflection angle are mixed with each other, so that it is hard to obtain sharp contrast.

When the refractive index of the transmission light dispersion layer is not in the above-described range, change of the hue is apt to become smaller. The thickness of the transmission light dispersion layer is preferably in the range from 10 to 50 nm. When the thickness of the transmission light dispersion layer is less than 10 nm, dispersion of light, when passing through the layer, is insufficient, and change of the hue becomes smaller, and on the contrary when the thickness is over 50 nm, feeling in touch of the cosmetics with this composite powder blended therein may become lower. It is to be noted that the quantity of the transmission light dispersion layer is preferably in the range from 1 to 40 weight portions against 100 weight portions of the ramentaceous substrate.

The transmission light dispersion layer is made from an inorganic oxide such as silica, or aluminum oxide, inorganic compounds such as magnesium fluoride, and organic resins such as polyamide, acryl, and polyurethane.

The composite powder according to the present invention should preferably have a reflective dispersion layer formed on the color layer which is the outermost layer and having the refractive index of 1.3 to 1.8 with fine irregularities on the surface. This reflective dispersion layer promotes dispersion of light with the irregularities on the surface thereof, and at the same time suppresses reflection of light on a surface of the particle, thus the effect of lowering the luster being provided. When the refractive index of the reflective dispersion layer exceeds 1.8, change of the hue is apt to become smaller. On the contrary, when the refractive index is less than 1.3, dispersion is insufficient, and the effect of lowering the luster may be insufficient.

Thickness of the reflective dispersion layer is preferably in the range from 10 to 100 nm. When the thickness is less than 10, dispersion of light is insufficient, and the effect of lowering the luster is apt to be insufficient, and on the contrary when the thickness is over 100 nm, the feeling in touch of the cosmetics with the composite powder blended therein becomes poorer, and also change of the hue is apt to become smaller.

A quantity of the light dispersion layer is preferably in the range from 3 to 20 weight portions against 100 weight portions of the composite powder before the light dispersion layer is formed thereon (namely, the ramentaceous substrate with the color layer, or the color layer and a reflective dispersion layer formed thereon).

When the quantity of the light reflection layer is less than 3 weight portions, dispersion of light is insufficient, and suppression of the luster may be insufficient, and on the contrary, when the quantity of the light dispersion layer is more than 20 weight portions, the feeling in touch of the cosmetics with the composite powder blended therein becomes poorer, and also change of the hue is apt to become smaller.

The light dispersion layer is made from an inorganic oxide such as silica or aluminum oxide, an inorganic compound such as magnesium fluoride, or organic resin such as polyamide, acryl, or polyurethane. Silica is especially preferable because it has a lower refractive index, and is adapted to coating.

An average particle diameter of the composite powder according to the present invention is in the range from 1 to 100 $\mu$m, and preferably in the range from 5 to 30 $\mu$m. The composite powder has a ramentaceous form like the substrate, and the average particle diameter is defined herein as the maximum length of the ramentaceous plane, and is calculated by measuring 100 composite powder pieces with a scanning electron microscope and calculating an average of the maximum lengths of the ramentaceous planes of the particles.

When the average particle diameter of the composite powder particles is less than 1 $\mu$m, the feeling in touch may be poor, and on the other hand, when the average particle diameter is over 100 $\mu$m, the luster is so intense that the natural appearance is lost. When the composite powder according to the present invention is blended in cosmetics, if the average particle diameter is in the range from 5 to 30 $\mu$m, cosmetics with excellent extendability on human skin and good feeling in touch can be obtained.

Further the thickness of the composite powder should preferably be in the range from 0.05 to 1 $\mu$m.

(2) Production of the Composite Powder

The method of producing the composite powder according to the present invention is described below.

Formation of the First Color Layer

To form the first color layer, any known coating method may be employed.

For instance, a metallic salt, an inorganic metal compound, and a partially hydrolyzed material thereof as a precursor of a color layer is added by a specified quantity to a dispersion of a ramentaceous substrate (the solvent is water and/or an organic solvent), hydrolysis or condensation/polymerization is performed under the existence of a catalyst for hydrolysis, if necessary, and the hydrolyte or condensed/polymerized material is deposited on the substrate.

Alternatively, a ramentaceous substrate is dispersed in a dispersion of a metallic salt, a solution of an organic metallic compound, or a partially hydrolyzed material thereof each as a precursor of a color layer, the resultant dispersion is hydrolyzed or further condensed/polymerized under the existence of a catalyst for hydrolysis, if necessary, and the hydrolyte or condensed/polymerized material is deposited on the substrate.

In addition, there can be enumerated the method of having color pigment powder deposited on a substrate by making use of static electricity and heating the deposited matter or the method of forming the first color layer by making use of the mechano-chemical method.

Also a method in which organic resin (monomer or oligomer such as polyamide or acryl is polymerized under the existence of a ramentaceous substrate to form an organic resin layer, and then the organic resin layer is colored with various types of pigments or dyes (coloring matters), or a method in which organic resin (monomer or oligomer) is polymerized with a ramentaceous substrate under the existence of pigments or paints is employable.

Still further a method in which fine particles of organic resin is deposited onto a substrate under the existence of various types of inorganic pigments or organic coloring matters by means of an electrostatic or a mechano-chemical method, or a method fine particles of organic resin is deposited as described above and then melted may be used.

Further a method in which a porous inorganic layer is formed on a ramentaceous substrate and then various types of paints or pigments are impregnated into the pores to form a color layer can be enumerated.

Formation of the Second and Subsequent Color Layers

The second and subsequent layers can be formed with the same method of forming the first color layer excluding the point that the ramentaceous substrate with the first color layer or the first color layer and the reflective dispersion layer formed thereon are used.

Formation of the Transmission Light Dispersion Layer

A known film forming method maybe used to form the transmission light dispersion layer.

For instance, in the case where the transmission light dispersion layer is an inorganic oxide, after the color layer is formed, a metal salt or an organic metallic compound or a partially hydrolyzed material thereof each as a precursor material of an inorganic oxide is added by a specified quantity, and then the added material is hydrolyzed or condensed/polymerized under the existence of a catalyst for hydrolysis, if necessary, and deposited on the substrate to form the transmission light dispersion layer.

When the transmission light dispersion layer is an inorganic compound salt (such as magnesium fluoride), a method in which powder of the inorganic compound salt is deposited on a substrate by making use of the static electricity and then the deposited matter is heated, or a mechano-chemical method may be employed.

Further, when the transmission light dispersion layer is organic resin, a method in which organic resin (monomer, oligomer) such as polyamide, or acryl is polymerized under the existence of a ramentaceous substrate with a color layer formed thereon, or a method in which fine particles of organic resin are deposited by means of the static electricity or a mechano-chemical method.

Formation of the Reflective Dispersion Layer

Also the reflective dispersion layer can be formed in the same way as that for forming the transmission light dispersion layer.

(3) Cosmetics

Cosmetics according to the present invention is described below.

In the cosmetics according to the present invention, the composite powder according to the present invention is blended together with various types of cosmetic components.

A blending rate of the composite power is preferably in the range from 1 to 90 weight percent. When the rate is less than 1 weight percent, the effect of providing natural appearance to a target body to be colored is hardly obtained. Namely, with the cosmetics according to the present invention, the hue changes according to a viewing angle, so that a three-dimensional effect can be given to a face or other solid portions of a human body irrespective of change in the brightness. When the blending rate is over 90 weight percent, the tinting power or oily feeling originally required to cosmetics may be lost.

The cosmetic components include, but not limited to, alcohols such as higher fatty alcohols, higher fatty acids, various types including ester oil, paraffin oil, and wax, ethylalcohol, propylene glycol, sorbitol, and glycerin; moisturizing agents such as muco-polysaccharides, collagens, PCA salt, lactates; various types of nonionic, cationic, anionic, or amphoteric surface surfactants; thickeners such as gum arabic, xanthane gum, polyvinyl pyrrolidone, etthylcellulose, carboxyl methylcellulose, carboxyvinyl polymer, denatured or not-denatured clay minerals; solvents such as ethyl acetate, acetone, and toluene; inorganic pigments/dyes; organic pigments/paints; antioxidants such as BHT, tocopherol; water; chemical agents; ultraviolet ray absorber; pH buffer; chelating agents; antiseptics; and perfumes. Further, at least one of inorganic fillers such as silica, talc, kaolin, and mica and physical pigments, and various types of organic resin may be contained therein.

When the composite powder according to the present invention is blended in cosmetics, the surface of the powder may be processed with, for instance, silicone or a fluorine compound.

The cosmetics according to the present invention can be manufactured by a known method, and is used in various forms including powder, cake-like, stick-like, pencil-like, liquid-phase, or cream-like forms, and more specifically the cosmetics include foundation, cream, emulsion, eye-shadow, make-up base, nail enamel, eye liner, mascara, lip stick, pack, and cosmetics for hair.

(4) Paints

Paints according to the present invention are described below.

The composite power according to the present invention is blended in the paints according to the present invention together with various types of paint components and various types of solvent components.

The blending rate of the composite powder is preferably in the range from 0.5 to 50 weight percent against the component for formation of paint film. When the blending rate is less than 0.5 weight percent, the natural appearance of the paint film is hardly obtained like in the case of the cosmetics, and on the other hand, when the blending rate is more than 50 weight percent, strength of the paint film may become lower and also flatness of the surface may easily be lost.

The components for formation of the paint film include, but not limited to, organic resin components such as acryl, vinyl chloride, polyurethane, nitrocellulose, and polyester, and inorganic components of metallic alkoxides such as organic titanate, and organic silicate. Further additives such as thickeners, ultraviolet absorbers, and stabilizers, and various types of coloring matters may be used. As solvent components of the paints, such materials as dimethylformamide, methylethylketone, and toluene may be used on the condition that the materials dissolve the components for formation of paint film.

DETAILED DESCRIPTION OF THE EMBODIMENTS

The present invention is described in detail with reference to the embodiments thereof.

Embodiment 1

100 g of mica with an average particle diameter of 12 $\mu$m was added to 1 liter of demineralized water and the resultant suspension was fully agitated and heated to 75° C. with the pH adjusted to 4.0. Then 250 g of ferric chloride solution corresponding to 10 weight percent $Fe_2O_3$ was added at the rate of 50 g/hour to the suspension maintaining the pH at 4.0 with 5% sodium hydroxide. After addition of the solution was over, the suspension was left as it was for 1 hour, and then a mixture of 209 g titanil sulfate aqueous solution corresponding to 10 weight percent $TiO_2$ and 11 g ferric chloride aqueous solution corresponding to 10 weight percent $Fe_2O_3$ was added to the suspension at the rate of 20 g/hour maintaining the pH at 4.0 with 5% sodium hydroxide. After addition of the aqueous solution was over, the suspension was left for 1 our as it was, and then cooled to the room temperature, filtered, and the filtrate was washed and dried for 100° C. for 15 hours, sintered for 3 hours under 750° C., and pulverized. When this powder was spread on black paper, it was found that the color was yellow at angular positions near the regular reflection angle and red brown at other points, and thus the hue changed according to a viewing angle and there was not excessive luster.

To assess change of the hue according to a viewing angle and the luster, the following measurement was performed. This inorganic composite powder was homogeneously spread over an adhesive surface of a transparent double-faced tape adhered on a non-luster white paper piece, and change of the color tone L*C*h* was measured with the three-dimensional declination spectroscope (manufactured by Murakami Shikisai Kenkyusho, GCMS-4 (double-beam system, light source: D65, viewing angle: 10°) under the conditions of incidence angle of 45° and receiving angle from −80° to 80° (at the interval of 5°). The result of measurement of the difference ($h_{MAX}-h_{MIN}$) between the maximum value $h_{MAX}$ and the minimum value $h_{MIN}$ is shown in Table 1. The ratio $L^*_{MAX}/L^*_{MIN}$ is shown in Table 2.

Embodiment 2

Like in Embodiment 1, after the substrate is coated with ferric oxide, the composite was filtered and washed, and then dried for 15 hours under the temperature of 100° C. and then sintered for one hour under the temperature of 800° C. and was pulverized. Then 100 g of the pulverized sample was added to 1 liter of demineralized water and the suspension was suspended. Then the suspension was heated to 80° C. with the pH adjusted to 9.0, and then 100 g sodium silicate aqueous solution corresponding to 10 weight percent $SiO_2$ was added to the suspension over about 5 hours maintaining the pH at 9.0 with aqueous solution of hydrochloric acid. After addition of the sodium silicate solution was over, the resultant suspension was left for 1 hour as it was, and filtered. The filtrate was washed and dried for 15 hours under the temperature of 100° C. to obtain inorganic composite powder in which mica was coated with ferric oxide and silica. 100 g of the sample was added to 1 liter of demineralized water, the suspension was fully agitated, and then a mixture of 171 g of titanil sulfate aqueous solution corresponding to 10 weight percent $TiO_2$ and 9 g of ferric oxide aqueous solution corresponding to 10 weight percent $Fe_2O_3$ was added to the suspension at the rate of 16 g/hour maintaining the pH at 4.0 with 5% sodium hydroxide aqueous solution. After addition of the mixture was over, the suspension was left for about 1 hour as it was, and then cooled to the room temperature and filtered, and then the filtrate was washed and dried for 15 hours under the temperature of 100° C., then sintered for 3 hours under 700° C., and was pulverized. When this powder was spread on black paper, it was found that the color was yellow at angular positions near the regular reflection angle and red brown at other points, and thus the hue changed according to a viewing angle and there was not excessive luster. The difference ($h_{MAX}-h_{MIN}$) and the ratio $L^*_{MAX}/L^*_{MIN}$ were measured like in the embodiment 1, and the results are shown in Table 1 and Table 2.

Embodiment 3

100 g of the inorganic composite power obtained in the embodiment 2 was added to a mixture of 100 g of 20 weight percent silica organosol dispersed 0.08 μm spherical silica in monoethylene glycol as a dispersion medium and 220 g of isopropanol, and 500 q ethanol was added to the resultant mixture solution agitating it under the room temperature adjusting the pH at 9.5 adding 28% ammonia water to have silica particles deposited on the inorganic composite particles. The composite powder was filtered, and the filtrate was dried for 20 hours under the temperature of 150° C. and then pulverized. When this powder was spread on black paper, it was found that the color was yellow at angular positions near the regular reflection angle and red brown at other points, and thus the hue changed according to a viewing angle and there was not excessive luster. The difference ($h_{MAX}-h_{MIN}$) and the ratio $L^*_{MAX}/L^*_{MIN}$ were measured like in the embodiment 1, and the results are shown in Table 1 and Table 2.

Embodiment 4

100 g of talc with an average particle diameter of 10 μm was added to 1 liter of demineralized water, and the suspension was fully agitated and then heated to 80° C. with the pH adjusted to 4.5. A mixed solution of 102 g aluminum chloride aqueous solution corresponding to 10 weight percent $Al_2O_3$ and 106 g cobalt chloride aqueous solution corresponding to 10 weight percent CoO was added to this suspension over about 5 hours maintaining the pH at 4.5 with 10 weight percent ammonia water. After addition was over, the mixed solution was left as it was for 1 hour, and filtered, and then the filtrate was washed and dried for 15 hours under the temperature of 100° C., and then sintered for 1 hour under the temperature of 850° C. and pulverized to obtain talc coated with blue aluminum oxide and cobalt oxide. 100 g of the talc was added to 1 liter of demineralized water and the suspension was agitated. This suspension was heated to 80° C. and the pH was adjusted to 9.0, and then 100 g sodium silicate corresponding to 10 weight percent $SiO_2$ was added to the suspension over about 5 hours maintaining the pH at 9.0 with a hydrochloric acid solution. After addition of the hydrochloride acid solution was over, the suspension was left for 1 hour as it was, and then cooled to the room temperature, and filtered. Then the filtrate was washed and dried over 15 hours under the temperature of 100° C. to obtain inorganic composite powder coated with aluminum oxide, cobalt oxide, and silica. 100 g of the inorganic composite powder was added to and mixed in 1 liter of demineralized water, and the mixed solution was heated to 70° C. to adjust pH 3.0 with 5% hydrochloric acid aqueous solution, and then 208 g of chromium solution corresponding to 10 weight percent chromium oxide was added over about 5 hours to the solution maintaining the pH with 10 weight % ammonia water. After addition of the chromium chloride was over, the suspension was left for 1 hour as it was and then filtered. The filtrate was washed and dried over 15 hours under the temperature of 100° C., and further sintered for 2 hours under the temperature of 600° C. and pulverized. When this powder was spread on black paper, it was found that the color was yellow at angular positions near the regular reflection angle and red brown at other points, and thus the hue changed according to a viewing angle and there was not excessive luster. The difference ($h_{MAX}-h_{MIN}$) and the ratio $L^*_{MAX}/L^*_{MIN}$ were measured like in the embodiment 1, and the results are shown in Table 1 and Table 2.

Embodiment 5

100 of the inorganic composite powder obtained in the embodiment 4 (talc coated with aluminum oxide, cobalt oxide, and silica) was added to and mixed in 1 liter of demineralized water, and a mixture of 171 g titanil sulfate aqueous solution corresponding to 10 weight percent $TiO_2$ and 9 g of ferric chloride aqueous solution corresponding to 10 weight percent $Fe_2O_3$ was added at the rate of 16 g/hour to the suspension maintaining the pH at 4.0 with 5% sodium hydroxide aqueous solution. After addition of the mixture was over, the suspension was left as it was for one hour, and then cooled to the room temperature and filtered. Then the filtrate was washed and dried for 15 hours under the temperature of 100° C., and further sintered for 3 hours under the temperature of 750° C. and pulverized. When this powder was spread on black paper, it was found that the color was yellow at angular positions near the regular reflection angle and nearly blue at other points, and thus the hue changed according to a viewing angle and there was not excessive luster. The difference ($h_{MAX}-h_{MIN}$) and the ratio $L^*_{MAX}/L^*_{MIN}$ were measured like in the embodiment 1, and the results are shown in Table 1 and Table 2.

Embodiment 6

100 g synthetic mica with an average particle diameter of 10 µ was added to 1 liter of demineralized water, and the suspension was fully agitated and heated to 75° C. with the pH adjusted to 4.0. Then 250 g of ferric chloride aqueous solution corresponding to 10 weight percent $Fe_2O_3$ was added to the suspension at the rate of 50 g/hour maintaining the pH at 4.0 with 5% sodium hydroxide aqueous solution. After addition of the solution was over, the suspension was left for 1 hour as it was and filtered. Then the filtrate was washed and dried for 15 hours under the temperature of 100° C., and further sintered for 2 hour under 800° C. and pulverized to obtain red mica coated with iron oxide. 60 g of the mica coated with iron oxide, 12 g PMMA (polymethyimethacrylate) with an average particle diameter of 0.2 µm and 3 g of tar coloring matter yellow No. 205 (Benzidine Yellow G) were previously mixed with each other, and organic and inorganic composite powder with the yellow PMMA layer formed on the iron oxide layer was obtained by using the mechano-fusion system (produced by Hosokawa Micron, AM-15F). The rotating speed of the rotor in this step was 1500 rpm. When this composite powder was spread over a black paper piece, it was found that red tint was obtained at angular positions near the regular reflection angle, skin color at angular positions slight displaced from the regular reflection angle, and yellow color at other points, and thus the color tone changed according to a viewing angle, and there was not excessive luster. The difference ($h_{MAX}-h_{MIN}$) and the ratio $L^*_{MAX}/L^*_{MIN}$ were measured like in the embodiment 1, and the results are shown in Table 1 and Table 2.

Embodiment 7

A polyurethane resin layer of mica coated with 20% polyurethane resin and having an average particle diameter of 15 µm was stained with Green No. 201 (alizanin cyanine green F) to obtain mica coated with bluish green polyurethane resin. 68 g of this polyurethane-coated mica and 7g of PMMA with an average particle diameter of 0.2 µm were previously mixed with each other, and at first the PMMA layer was coated using a mechano-fusion system (manufactured by Hosokawa Micron, AM-15F). The rotating speed of the rotor in this step was 1200 rpm. 65 g of this powder, 10 g of PMMA with an average particle diameter of 0.2 µm, and 5 g of red No. 226 (Helidone Pink CN) were previously mixed with each other, and a red PMMA layer was further coated by using the same mechano-fusion system. As a result, mica coated with a bluish green polyurethane resin layer, an achromatic PMMA layer, and a red PMMA layer was obtained. When the composite power was spread on a black paper piece, it was found that strongly bluish color was generated at angular positions near the regular reflection angle, purple color at angular positions slight far from the regular reflection angle, and red color at other positions, and thus the color tone changed according to a viewing angle, and there was no excessive luster. The difference ($h_{MAX}-h_{MIN}$) and the ratio $L^*_{MAX}/L^*_{MIN}$ were measured like in the embodiment 1, and the results are shown in Table 1 and Table 2.

Embodiment 8

Cake-like foundation containing the following components was prepared by using the inorganic composite powder obtained in Embodiment 3.

| | | |
|---|---|---|
| (1) | Inorganic composite powder | 25 |
| (2) | Serisite | 41 |
| (3) | Mica | 10 |
| (4) | Titanium oxide as pigment | 5 |
| (5) | Iron oxide (red) | 0.2 |
| (6) | Iron oxide (yellow) | 1.8 |
| (7) | Iron oxide (black) | 0.05 |
| (8) | Sorbitan fatty acid ester | 2.5 |
| (9) | Stearil alcohol | 6.0 |
| (10) | Lanolin | 5.0 |
| (11) | Fluidized paraffin | 2.0 |
| (12) | Triethanol amine | 1.0 |
| (13) | Methylparaben | 0.45 |
| (14) | Perfume | As required |

At first, a mixture of components (1) to (7) is prepared. Then the components (8) to (14) were heated to 70° C. and fully mixed with each other, and the resultant mixture was mixed with the above-described mixture and mixed to a homogeneous state. The resultant mixture was pulverized to obtain homogeneous particles and then compressed into a required form.

The obtained cake-like foundation was actually applied to a human skin to find that yellowish color was observed at angular positions near the regular reflection angle and dark red tint at other positions. In addition this cake-like foundation was actually applied to a face to find that the nose looked shapely and a cubic sense of the entire face was emphasized.

Embodiment 9

Eye-shadow containing the following components was prepared by using the composite powder obtained in the embodiment 4.

| | | |
|---|---|---|
| (1) | Composite powder | 45.0 |
| (2) | Serisite | 30.0 |
| (3) | Talc | 14.4 |
| (4) | Titanium oxide | 1.0 |
| (5) | Magnesium stearate | 3.0 |
| (6) | Fluidized paraffin | 4.0 |

| (7) 2-ethyl cetylhexanate | 2.5 |
| (8) Antiseptics | 0.1 |

At first, a mixture of components (1) to (5) was prepared. Then the components (6) to (8) were homogeneously mixed with each other, and the resultant mixture was homogeneously mixed with the mixture of components (1) to (5) The resultant mixture was pulverized to obtain particles with a homogeneous diameter, which were compressed to a desired form.

The obtained eye-shadow was actually applied to a human skin to find that green tint was observed at angular positions near the regular reflection angle and bluish color was observed at other positions. The eye-shadow was actually applied to eyelid to find that the color tone changed from green to blue according to a viewing angle to the face.

Embodiment 10

Paint containing the following components was prepared with the organic and inorganic composite powder obtained in Embodiment 6.

(1) Organic/inorganic composite powder 5.0

(2) Clear lacquer (produced by Endo Kagaku Kogyosho) 95.0

The components (1) and (2) were mixed with each other, and the inorganic and organic composite powder was homogeneously dispersed with a disperser based on the ultrasonic transmission system. This paint was spread over a white plate and fully dried, and the appearance was observed to find that the color tone changed from red to yellow according to a viewing angle.

Control 1

100 g of mica with an average particle diameter of 12 μm was added to 1 liter of demineralized water and the suspension was fully agitated and heated to 75° C. with the pH adjusted to 4.0. Then 250 g ferric chloride aqueous solution corresponding to 10 weight percent $Fe_2O_3$ was added at the rate of 50 g/hour to the suspension maintaining the pH at 4.0 with 5% sodium hydroxide aqueous solution. After addition of the solution was over, the suspension was left for 1 hour as it was, and filtered. Then the filtrate was washed and dried, and then sintered for 3 hours under the temperature of 800° C., and pulverized. The difference ($h_{MAX}-h_{MIN}$) and the ratio $L*_{MAX}/L*_{MIN}$ of this mica covered with ferric oxide were measured like in the embodiment 1, and the results are shown in Table 1 and Table 2. The result shows that the hue changed little.

Control 2

The difference ($h_{MAX}-h_{MIN}$) and the ratio $L*_{MAX}/L*_{MIN}$ of this mica covered with iron oxide obtained in the same way as in Embodiment 6 excluding the point that mice with an average particle diameter of 37 μm was used, and the result is shown in Table 1 and Table 2. The result shows that the hue changes a little but the luster is too strong and provides the unnatural appearance.

Control 3

The difference ($h_{MAX}-h_{MIN}$) and the ratio $L*_{MAX}/L*_{MIN}$ of the blue talc coated with aluminum oxide and cobalt oxide obtained in Embodiment 4 were measured in the same way as the embodiment 1, and the result is shown in Table 1 and Table 2. The result shows that the hue changes little.

Control 4

100 g mica with an average particle diameter of 12 μm was added to 1 liter of demineralized water, and the suspension was fully agitated, and heated to 75° C. with the pH adjusted to 4.0. A mixture of 209 g titanil sulfate corresponding to 10 weight percent $TiO_2$ and ferric chloride aqueous solution corresponding to 10 weight percent $Fe_2O_3$ was added to this suspension at the rate of 20 g/hour maintaining the pH at 4 0 with 5% sodium hydroxide aqueous solution. After addition of the mixture was over, the suspension was left as it was for 1 hour, and then cooled to the room temperature, and filtered. The filtrate was washed and dried for 15 hours under the temperature of 100° C., and further sintered for 3 hours under 750° C., and pulverized. The difference ($h_{MAX}-h_{MIN}$) and the ratio $L*_{MAX}/L*_{MIN}$ of the obtained titanium oxide containing iron oxide were measure, and the result is shown in Table 1 and Table 2. The result shows that the hue changes little.

Control 5

The difference ($h_{MAX}-h_{MIN}$) and the ratio $L*_{MAX}/L*_{MIN}$ of the bluish green polyurethane resin-coated mica obtained in the embodiment 7 were measured in the same way as the embodiment 1, and the result is shown in Table 1 and Table 2. The result shows that the hue changes little.

Control 6

After the mica was coated with ferric oxide like in the embodiment 1, a mixed aqueous solution of 110 g titanil sulfate aqueous solution corresponding to 10 weight percent $TiO_2$ and 110 g ferric chloride aqueous solution corresponding to 10 weight percent $Fe_2O_3$ was added at the rate of 20 g/hour maintaining the pH at 4.0 with 5% sodium hydroxide. After addition of the mixed aqueous solution was over, the suspension was left as it was for one hour, cooled to the room temperature, and filtered. When the filtrate was washed and dried for 15 hours under the temperature of 10020 C., and further sintered for 3hours under 750° C. and pulverized. When this powder was spread over a black paper piece, it was found that red brown color was observed at angular positions near the regular reflection angle and also the same color at other positions and thus the hue changed little according to a viewing angle. The difference ($h_{MAX}-h_{MIN}$) and the ratio $L*_{MAX}/L*_{MIN}$ were measured like in the embodiment 1, and the result is shown in Table 1 and Table 2. In this control, content of iron oxide in the iron oxide-containing titanium which is the second layer is high, and the component generates strong brown color, which makes the difference in hue from the iron oxide layer which is the first color layer smaller, so that the hue changes little according to a viewing angle.

Control 7

114 g of flake-like aluminum powder with an average particle diameter of about 60 μm and thickness of 0. 5 μm was dispersed in 2 liters of ethanol, and heated to 45° C. 28 weight % ammonia water was added to this suspension to adjust the pH to 10.0, and under the conditions, tetraethoxysilane corresponding to 86 g of $SiO_2$ and 28 weight percent ammonia water were added to the suspension. After addition of the mixture was over, the suspension was further agitated for additional two hours, and filtered. Then the filtrate was washed, dried under 110° C. 100 g of this silica-coated flake-like aluminum was added to 1 liter of demineralized water, and the suspension was fully agitated and then heated to 750° C. with the pH adjusted to 4.0. 140 g of ferric chloride aqueous solution corresponding to 10 weight percent $Fe_2O_3$ was added to this suspension at the rate of 20 g/hour maintaining the pH at 4.0 with 5 weight % sodium hydroxide aqueous solution. After addition of the ferric chloride aqueous solution was over, the suspension was left as it was for 1 hour, cooled to the room temperature and filtered. Then the filtrate was washed, dried for 15 hours under the temperature of 100° C., and sintered for 3 hours under the temperature of 500° C., and pulverized.

This powder had strong metallic luster, and when spread on a black paper piece, shows golden color at positions near the regular reflection angle and redish color at other angular positions. In this control, as a flake-like metal was used as a substrate, the color tone changes at angular positions near the regular reflection angle and other angular positions because of strong regular reflection on the mirror surface reflectivity, but the appearance was unnatural due to the strong metallic luster and its opacity. The difference ($h_{MAX}-h_{MIN}$) and the ratio $L^*_{MAX}/L^*_{MIN}$ were measured like in the embodiment 1, and the result is shown in Table 1 and Table 2.

TABLE 1

|  | $h_{MAX}$ | Receiving angle | $h_{MIN}$ | Receiving angle | $h_{MAX} - h_{MIN}$ |
|---|---|---|---|---|---|
| Embodiment 1 | 64.7 | 25 | 49.2 | −70 | 15.5 |
| Embodiment 2 | 67.6 | 25 | 53.5 | −80 | 14.1 |
| Embodiment 3 | 64.5 | 20 | 51.7 | −75 | 12.8 |
| Embodiment 4 | 210.1 | −75 | 192.3 | 30 | 17.8 |
| Embodiment 5 | 281.1 | −70 | 78.3 | 20 | 157.2 |
| Embodiment 6 | 78.5 | −70 | 60.8 | 20 | 17.7 |
| Embodiment 7 | 324.3 | −70 | 298.4 | 15 | 25.9 |
| Control 1 | 49.7 | 25 | 46.8 | −20 | 2.8 |
| Control 2 | 58.1 | 35 | 48.3 | −65 | 9.8 |
| Control 3 | 221.3 | −30 | 218.2 | 25 | 3.1 |
| Control 4 | 60.1 | 30 | 54.1 | −70 | 6.0 |
| Control 5 | 253.3 | −30 | 250.2 | 40 | 2.8 |
| Control 6 | 60.3 | −65 | 59.0 | 25 | 1.3 |
| Control 7 | 87.3 | 45 | 25.3 | −55 | 62.0 |

TABLE 2

|  | $L^*_{MAX}$ | Receiving angle | $L^*_{MIN}$ | Receiving angle | $L^*_{MAX}/L^*_{MIN}$ |
|---|---|---|---|---|---|
| Embodiment 1 | 91.3 | 45 | 47.7 | −65 | 1.91 |
| Embodiment 2 | 79.0 | 40 | 44.7 | −65 | 1.77 |
| Embodiment 3 | 72.0 | 40 | 47.0 | −65 | 1.53 |
| Embodiment 4 | 63.1 | 40 | 43.2 | −70 | 1.46 |
| Embodiment 5 | 77.8 | 40 | 45.1 | −65 | 1.73 |
| Embodiment 6 | 70.9 | 40 | 50.2 | −65 | 1.41 |
| Embodiment 7 | 58.4 | 35 | 50.5 | −65 | 1.16 |
| Control 1 | 82.3 | 40 | 41.2 | −70 | 2.00 |
| Control 2 | 95.8 | 45 | 32.8 | −65 | 2.92 |
| Control 3 | 65.3 | 40 | 43.2 | −65 | 1.51 |
| Control 4 | 90.8 | 45 | 49.3 | −65 | 1.84 |
| Control 5 | 60.3 | 40 | 50.1 | −65 | 1.20 |
| Control 6 | 89.6 | 40 | 45.3 | −65 | 1.98 |
| Control 7 | 98.9 | 45 | 22.3 | −70 | 4.43 |

What is claimed is:

1. Composite powder comprising: a ramentaceous substrate selected from the group consisting of a natural mineral and an inorganic oxide, and at least two, distinct and sequential color layers coated on the ramentaceous substrates, wherein a difference ($h_{MAX}-h_{MIN}$) between a maximum value hex and a minimum value $h_{MIN}$ of an ab hue angle $h_{ab}$ as defined in Recommendation on Uniform Color Space by CIE is in a range from 100 to 180° and in case a value of the difference is over 180°, the value of $360°-(h_{MAX-hMIN})$ is in a range from 100 to 180, and a ratio of a maximum value vs a minimum value of brightness $L^*$ as defined in the Recommendation is in a range from 1.0 to 2.0 to thereby provide a color tone changing according to a viewing angle, and a transmission light dispersion layer having a refractive index in a range from 1.3 to 1.8, wherein said dispersion layer is located between the color layers.

2. A composite powder according to claim 1, further comprising a reflective dispersion layer coated on a surface of the composite powder, said reflective dispersion layer having a refractive index in a range from 1.3 to 1.8.

3. A composite powder according to claim 1, wherein the natural mineral is selected from the group consisting of mica, talc, and sericite.

4. A composite powder according to claim 1, wherein the inorganic oxide is selected from the group consisting of synthetic mica, synthetic sericite, silica in a plate form, aluminum oxide in a plate form and titanium oxide in a plate form.

5. A cosmetic composition comprising the composite powder according to claim 1.

6. A cosmetic composition comprising the composite powder according to claim 2.

7. A paint composition comprising the composite powder according to claim 1.

8. A paint composition comprising the composite powder according to claim 2.

9. A composite powder consisting essentially of:

a ramentaceous substrate selected from the group consisting of a natural mineral and an inorganic oxide, and at least two, distinct and sequential color layers coated on the ramentaceous substrate, wherein a difference ($h_{max}-h_{min}$) between a maximum value $h_{max}$ and a minimum value $h_{min}$ of an ab hue angle $h_{ab}$ as defined in Recommendation on Uniform Color Space by CIE is in a range from 10° to 180°, and in case a value of the difference is over 180°, the value of $360°-(h_{max}-h_{min})$ is in a range from 10° to 180°, and a ratio of a maximum value vs a minimum value of brightness $L^*$ as defined in the Recommendation is in a range from 1.0 to 2.0 to thereby provide a color tone changing according to a viewing angle, and a transmission light dispersion layer having a refractive index in a range from 1.3 to 1.8, wherein said dispersion layer is located between the color layers.

10. A composite powder according to claim 9, wherein the natural mineral is selected from the group consisting of mica, talc, and sericite.

11. A composite powder according to claim 9, wherein the inorganic oxide is selected from the group consisting of synthetic mica, synthetic sericite, silica in a plate form, aluminum oxide in a plate form and titanium oxide in a plate form.

12. A composite powder consisting essentially of:

a ramentaceous substrate selected from the group consisting of a natural mineral and an inorganic oxide, and at least two, distinct and sequential color layers coated on the ramentaceous substrate, wherein a difference ($h_{max}-H_{min}$) between a maximum value $h_{max}$ and a minimum value $h_{min}$ of an ab hue angle $h_{ab}$ as defined in Recommendation on Uniform Color Space by CIE is in a range from 10° to 180° and in case a value of the difference is over 180°, the value of 360°−($h_{max}$−$h_{min}$) is in a range from 100 to 180°, and a ratio of a maximum value vs a minimum value of brightness L* as defined in the Recommendation is in a range from 1.0 to 2.0 to thereby provide a color tone changing according to a viewing angle, and a transmission light dispersion layer having a refractive index in a range from 1.3 to 1.8, wherein said dispersion layer is located between the color layers, and a reflective dispersion layer coated on a surface of the composite powder, said reflective dispersion layer having a refractive index in a range from 1.3 to 1.8.

13. A composite powder according to claim 12, wherein the natural mineral is selected from the group consisting of mica, talc, and sericite.

14. A composite powder according to claim 12, wherein the inorganic oxide is selected from the group consisting of synthetic mica, synthetic sericite, silica in a plate form, aluminum oxide in a plate form and titanium oxide in a plate form.

* * * * *